United States Patent [19]
Kosaka et al.

[11] Patent Number: 5,469,251
[45] Date of Patent: Nov. 21, 1995

[54] APPARATUS FOR DETECTING FLUORESCENCE OF PARTICLES IN A FLUID AND ANALYZING THE PARTICLES

[75] Inventors: Tokihiro Kosaka, Kakogawashi; Shinichi Ogino, Nishiku; Yasunori Maekawa, Mikishi, all of Japan

[73] Assignee: Toa Medical Electronics Co., Ltd., Kobe, Japan

[21] Appl. No.: 70,667

[22] Filed: Jun. 2, 1993

[30] Foreign Application Priority Data

Jun. 12, 1992  [JP]  Japan ............................. 4-179297

[51] Int. Cl.$^6$ .................... G01N 15/14; G01N 21/53; G01N 33/48; G01N 21/64
[52] U.S. Cl. ............... 356/73; 356/39; 356/336; 356/317
[58] Field of Search ............... 356/73, 39, 335, 356/336, 339, 337, 338, 343, 400, 317, 318; 250/458.1

[56] References Cited

U.S. PATENT DOCUMENTS

| | | | |
|---|---|---|---|
| 4,732,477 | 3/1988 | Tanaka et al. | 356/336 |
| 5,047,963 | 9/1991 | Kosaka | 356/336 |
| 5,050,987 | 9/1991 | Kosaka | 356/39 |
| 5,159,397 | 10/1992 | Kosaka et al. | 356/39 |
| 5,159,642 | 10/1992 | Kosaka | 356/39 |
| 5,191,388 | 3/1993 | Kilham | 356/335 |

*Primary Examiner*—Robert P. Limanek
*Assistant Examiner*—Alexander Oscar Williams
*Attorney, Agent, or Firm*—Jones & Tullar & Cooper

[57] ABSTRACT

An apparatus for analyzing particles at high precision capable of obtaining informations in real time such as morphological informations and fluorescence image of cells (particles) contained in a sample liquid such as blood and urine. It comprises a flow cell (18) for forming a flat sample liquid flow (20), a light source (10) for emitting light to the sample liquid flow, an image intensifier (34) for amplifying particle fluorescence image emitted from the broader side of the sample liquid flow, a line sensor (36) for scanning the fluorescence image amplified by the image intensifier and issuing imaging signal (Sf (i)) in every scanning i, and a signal processing device (42) for processing signals or operating on the basis of the imaging signal (Sf (i)) from the line sensor.

7 Claims, 9 Drawing Sheets

(FLUORESCENCE IMAGE If)

(TRANSMITTED LIGHT IMAGE It)

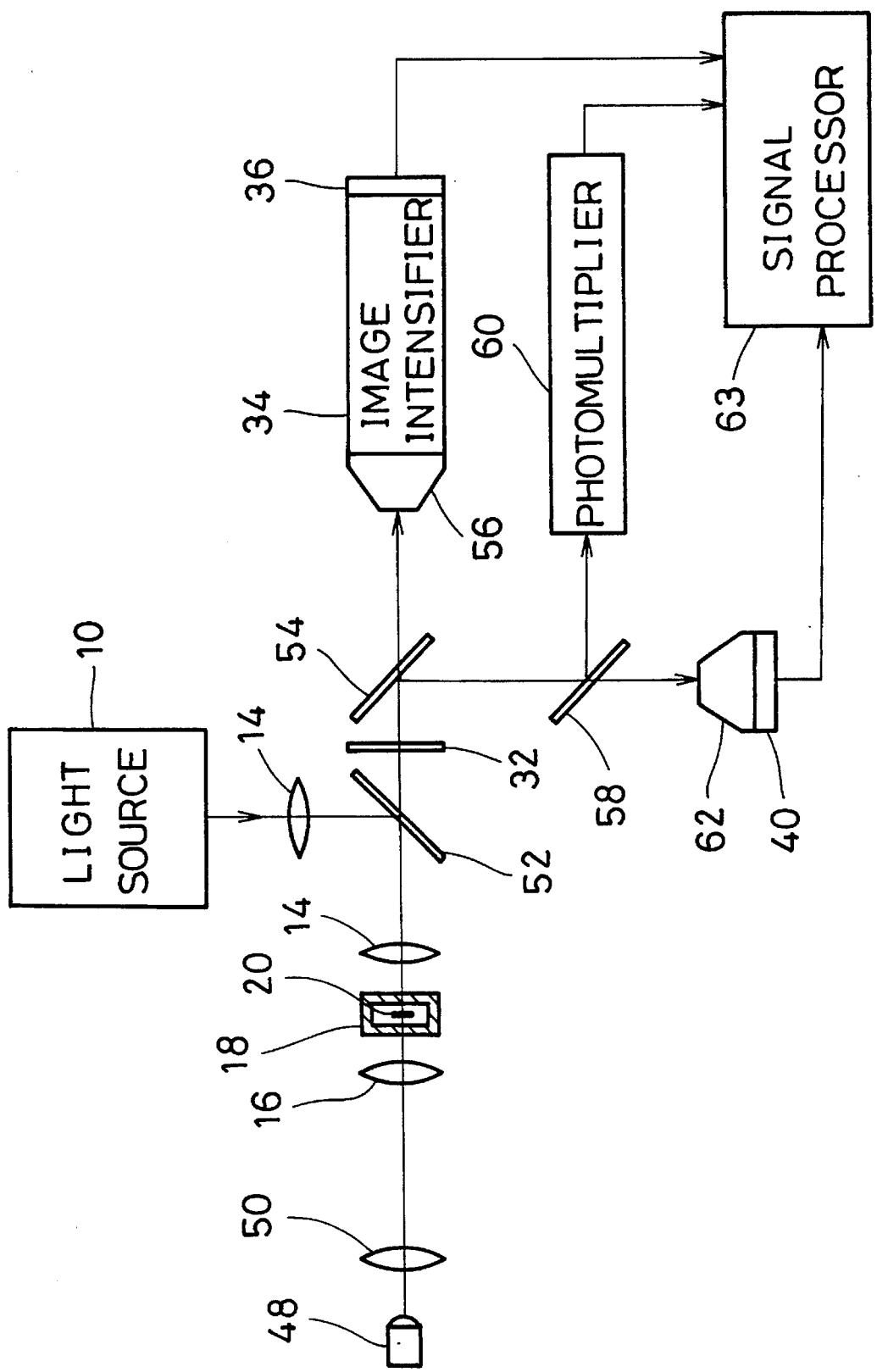

APPARATUS FOR DETECTING FLUORESCENCE OF PARTICLES IN A FLUID AND ANALYZING THE PARTICLES

BACKGROUND OF THE INVENTION

The present invention relates to an apparatus for analyzing particles for obtaining parameters relating to fluorescence (cumulative fluorescent intensity, area or roundness, degree of fluorescent emission portion, etc.), on the basis of fluorescence image signals from cells (particles) contained in a sample liquid such as blood and urine, and more particularly to an apparatus for analyzing particles to detect and analyze the fluorescence of cells stained by a fluorescent dye, by irradiating (illuminating) laser light for exciting fluorescence to a flat sample liquid flow in a flow cell for forming a flat sheath flow.

Relating to the apparatus of the present invention, hitherto is known an apparatus in a construction designed for obtaining more specific morphological (morphologic) information for individual particles, on the basis of optical signals obtained from parts of the particles to be analyzed, by optically scanning particles flowing in a sheath flow with a fine focused laser beam in the direction crossing the flow direction of the particles.

This conventional apparatus for analyzing particles employing a flow cell is constructed as shown in FIG. 1, in which a laser beam from a laser light source 100 is focused finely and irradiated to particles flowing in a sheath flow in a flow cell 106 in two dimensions is not obtained. That is, it does not possess resolution ability in the right angle direction to the particle flow direction, as compared with the method shown in FIG. 1 or the apparatus of the present invention described below, the information obtained about the particles is less, and precision is low.

On the other hand, the Japanese Laid-open Patent Hei. 1-270644 discloses an apparatus for analyzing particles capable of obtaining particle image information by scanning with a light beam in a direction crossing the passing (transmitting) direction of the particles, and detecting the light passing through the particles by a photo detector.

The Japanese Laid-open Patent Hei. 2-105041 is an improved version of the apparatus disclosed in the above patent 1-270644, and discloses an apparatus for measuring particles capable of receiving transmitted light by an array type photo detector disposed at a conjugate position with the particle to be detected.

The Japanese Laid-open Patent Sho. 52-113272 discloses an apparatus capable of obtaining chrominance (color) information and morphological information (area and shape) of cells, by scanning with a spot light using a flying spot tube, in the midst of passing of biological cell specimen through a flow cell.

According to the Japanese Laid-open Patent Sho. 62-254037, the flow cytometer is furnished with a streak imaging device, and detection of particles by this imaging device are executed almost simultaneously, and the imaging signal is processed only when matched with the predetermined characteristic value, that is, only particles with specific characteristic are imaged. As the imaging device, sampling imaging by using a one-dimensional image sensor is also disclosed.

The Japanese Laid-open Patent Hei. 3-123840 discloses a construction designed for determining a particle size distribution of an object on the basis of the two-dimensional image data obtained by imaging a moving object such as iron ore by a one-dimensional image sensor, and accumulating the one-dimensional image data.

In the U.S. Pat. No. 4,338,024 and the corresponding Japanese Patent Publication Hei. 3-52573, a flat sample liquid flow is formed, that is, a flat sheath flow is formed, and the particle image is taken.

The Japanese Patent Publication Sho. 63-22569 discloses an imaging method in an image fiber transmission path for enlarging or reducing a synthetic image at the reception side, by enlarging or reducing while keeping spatial distributions at both ends of an image fiber in similar forms (figure).

In the catalogue (J9011-29AOIOM) of fused optical fibers of HOYA-SCHOTT Co., optical fibers capable of enlarging and reducing taper-shaped images, and image processing using an image amplifier, tapered optical fiber, and CCD are disclosed.

The Japanese Laid-open Patent Hei. 2-196983 discloses a laser light source apparatus designed to focus (condense) an output light of a laser diode by using an optical fiber.

In the Japanese Laid-open Patents Hei. 4-72544 and Hei. 4-72545, a second light source (normally emitting) for particles, and imaging means (one-dimensional image sensor) aside from a first light source (pulse emission) for imaging particles, and imaging means (two dimensional image sensor) are used. In the disclosed apparatus for analyzing particle images, the second imaging region is in a line form, and the light from the second light source is emitted to the imaging region in a long elliptical form.

In these conventional general flow cytometers, the intensity of fluorescence emitted from the cell stained by a fluorescent dye is easily determined (obtained), but information about the fluorescence images such as fluorescence luminance distribution and area and roundness degree of fluorescent emission portion cannot be obtained.

In the apparatuses disclosed in the Japanese Laid-open Patents Hei. 1-270644, Hei. 2-105041 and Sho. 52-113272, since an optical beam is used in scanning, a special device is needed, and stable scanning is difficult.

The apparatus disclosed in the Japanese Laid-open Patent Hei. 3-123840 relates to an apparatus for measuring the particle size of iron ore or other materials charged into a blast furnace, the field of which is different from the present invention. Besides, nothing is mentioned about real time processing of accumulated image data, or determination (calculation) of parameters of area, roundness degree, luminance distribution, etc.

The Japanese Laid-open Patents Sho. 62-254037 and Hei. 3-123840 do not refer to flat passing of sample liquid flow. By forming a flat flow, the quantity of analysis can be increased.

In the U.S. Pat. No. 4,338,024 and the Japanese Patent Publication Hei. 3-52573, as mentioned above, forming of a flat sample liquid flow is mentioned, but the construction "comprising means for forming a flat sample liquid flow, a one-dimensional image sensor for issuing an imaging signal in every scanning, and processing means for processing signals and operating onn the basis of the imaging signals from the sensor" is not stated in any one of these seven publications.

Besides, in the Japanese Patent Publication Sho. 63-22569 and in the catalogue of fused optical fibers of HOYA-SCHOTT Co., use in the particle analyzing field is not mentioned.

The Japanese Laid-open Patent Hei. 2-196983 states nothing about use in the particle analyzing field by lowering the coherency of laser light.

The Japanese Laid-open Patents Hei. 4-72544 and Hei. 4-72545 disclose nothing about acquisition of more specific fluorescence information and morphological information of particles on the basis of imaging signals from the one-dimensional image sensor by scanning particles.

OBJECT AND SUMMARY OF THE INVENTION

It is hence a primary object of the present invention to provide an apparatus for analyzing particles of higher precision, capable of obtaining more specific morphological information or fluorescence information of particles in real time, in addition to optical features of the particles (scattered light intensity, fluorescence intensity, etc.) obtained in the conventional apparatus.

The apparatus for analyzing particles of the present invention is constructed to obtain information of individual cells, such as cumulative fluorescence intensity, area and roundness degree of fluorescent emission portion and fluorescence luminance distribution, in real time, by amplifying the fluorescence emitted from cells by an image intensifier, scanning the fluorescence images by an image sensor (for example, line sensor), and processing the thus obtained detection signals.

To achieve the noted object, the present invention provides, as shown in FIG. 2, an apparatus for analyzing particles by discharging a sample liquid containing particles to be detected from a nozzle of a flow cell, passing a sheath liquid around the sample liquid to form a sheath flow, emitting light to the sample liquid flow, detecting the light from particles, and analyzing particles according to the detection signals, comprising:

a flow cell for forming a sample liquid flow of a flat flow thin in thickness and broad (wide) in width, a light source for emitting light to the sample liquid, an image intensifier for intensifying (amplifying) the particle fluorescence image excited by the light and emitted from the broad side of the sample liquid flow on the input plane of the image intensifier, a one-dimensional image sensor extended at the output plane side of the image intensifier in a direction vertical to the flow direction of particles, for scanning the fluorescence image amplified by the image intensifier, and issuing an imaging signal Sf (i) at every scanning i, and signal processing means for processing signals or/and operating on the basis of the imaging signal Sf (i) from the one-dimensional image sensor.

In another apparatus of the present invention, in the above apparatus as shown in FIG. 2, a second one-dimensional image sensor is provided, being extended in a direction vertical to the flow direction of the particles, for scanning the particle transmitted light images of the broader side of the sample liquid flow, and issuing an imaging signal St (i) in every scanning i.

In another apparatus of the present invention, in the above apparatus as shown in FIG. 2, means (e.g. optical fiber) for lowering the coherency of emitted light is provided.

In another apparatus of the invention, in the above apparatus as shown in FIG. 2, an image fiber is provided to deepen the focal depth (depth of a focus) of the particle image.

The present invention also provides a different apparatus as shown in FIG. 3, which is an apparatus for analyzing particles by discharging a sample liquid containing particles to be detected from a nozzle of a flow cell, passing a sheath liquid around the sample liquid to form a sheath flow, emitting light to the sample liquid flow, detecting the light from particles, and analyzing particles according to the detection signals, comprising:

a flow cell for forming a sample liquid flow of a flat flow thin in thickness and broad (wide) in width, a first light source for emitting first light to the sample liquid, an image intensifier for intensifying (amplifying) the particle fluorescence image excited by the first light and emitted from the broader side of the sample liquid flow on an input plane of the image intensifier, a first one-dimensional image sensor extended at the output plane side of the image intensifier for scanning the fluorescence image amplified by the image intensifier and issuing an imaging signal Sf (i) in every scanning i, a second light source for emitting second light different in wavelength from the first light to the sample liquid, a second one-dimensional image sensor extended in a direction vertical to the particle flow direction for scanning the particle transmitted light image of the broader side of the sample liquid flow and issuing an imaging signal St (i) in every scanning i, and signal processing means for processing signals and/or operating on the basis of the imaging signal Sf (i) from the first one-dimensional image sensor and the imaging signal St (i) from the second one-dimensional image sensor.

In another apparatus of the present invention, in the above apparatus as shown in FIG. 3, the second light source is a light source for emitting low coherency light.

In another apparatus of the invention, in the above apparatus as shown in FIG. 3, image fibers are provided in order to deepen the focal depth (depth of a focus) of particle image.

In another different apparatus of the invention, in the above apparatus as shown in FIG. 2 and FIG. 3, the signal St (i) from the one-dimensional image sensor is processed, and the image intensifier is controlled so as to be in active state only while a particle is passing through imaging region A2.

BRIEF DESCRIPTION OF THE DRAWINGS

FIG. 10 is a schematic diagram (plan) showing a further different embodiment of an apparatus for analyzing particles of the present invention.

DETAILED DESCRIPTION OF THE PREFERRED EMBODIMENTS

Figure 1:
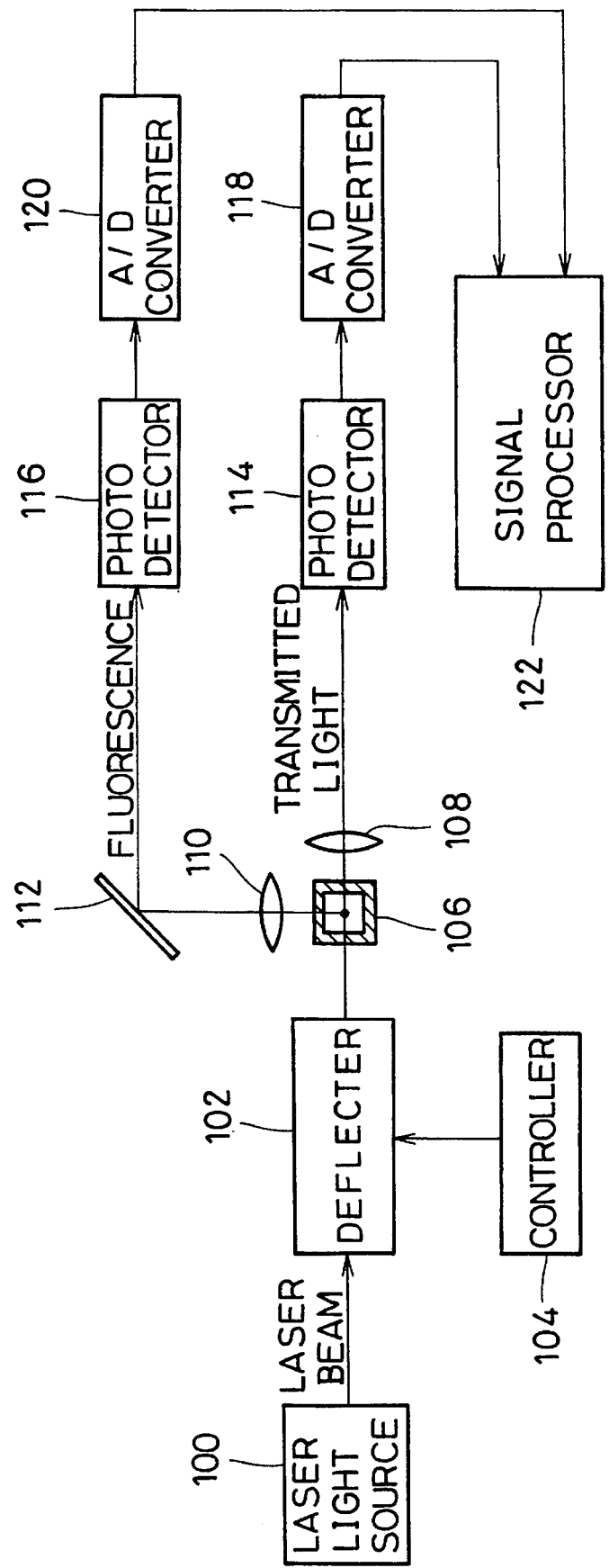
FIG. 1 is a schematic diagram (plan) showing an example of a conventional apparatus for analyzing particles.

Referring now to the drawings, some of the preferred embodiments of the invention are described in detail below.

Embodiment 1

Figure 2:
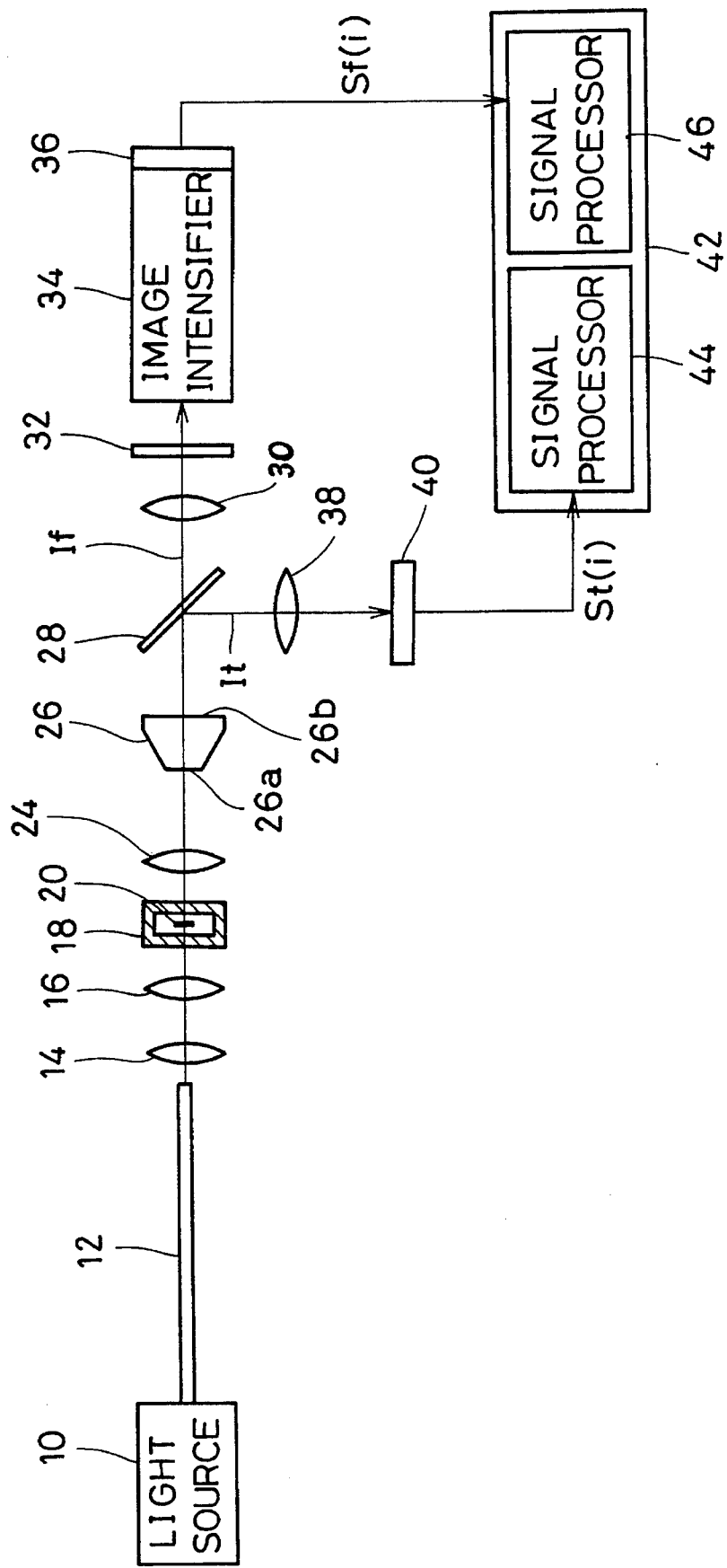
FIG. 2 is a schematic diagram (plan) showing an embodiment of an apparatus for analyzing particles of the present invention.

FIG. 2 shows an apparatus for analyzing particles in Embodiment 1. A sample liquid flow (sample flow) 20 containing particles to be detected is led into a flow cell 18 made of a transparent material such as glass or plastic, and a sheath liquid is supplied so as to cover the surroundings of the sample flow, so that a sheath flow is formed.

The sample flow in the flow cell 18 in the apparatus shown in FIG. 2 is, different from the conventional flow cytometer, designed to flow thinly in the optical axis direction of the emitted laser light, and broadly in the vertical (right-angled) direction to the laser optical axis. That is, the diluted and dyed sample is led into the flat sheath flow cell 18, and a flat sample flow 20 is formed. The light from a laser light source 10 is first led into an optical fiber 12 to lower the coherency. This light is processed (formed) by a cylindrical lens 14 and a condenser lens 16 so as to be thin in the particle flowing direction, and broad in the vertical (right-angled) direction to the flow direction, and is emitted to the sample flow.

Figure 4:
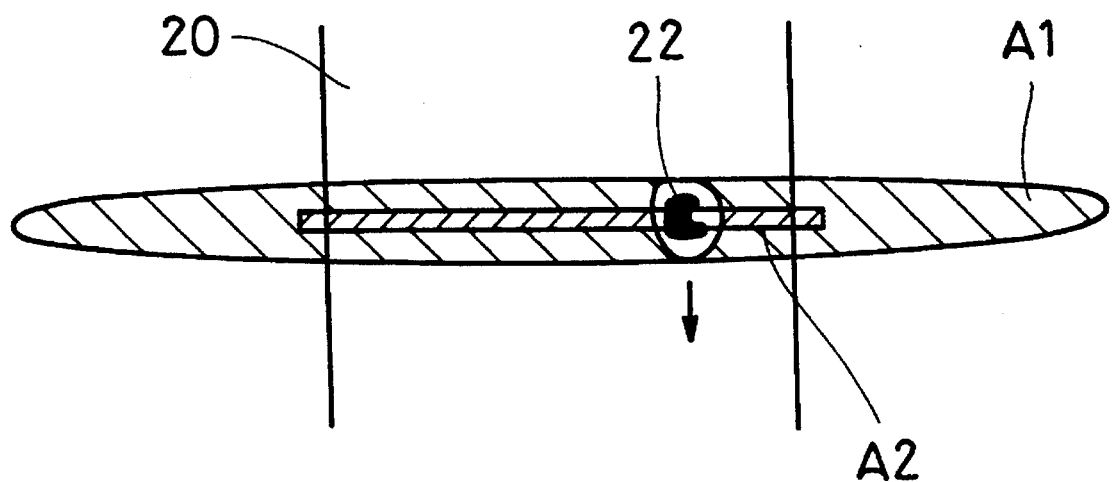
FIG. 4 is an explanatory view showing a beam emitting area and imaging area of a one-dimensional image sensor (line sensor) in FIG. 2 and FIG. 3.

FIG. 4 shows an irradiation area of laser light as seen from the direction of the optical axis. As shown in FIG. 4, the imaging area A2 of the line sensor is placed in the center of the light source irradiation area A1. Numeral 22 is a particle.

The fluorescence from the particle 22 illuminated with laser light is collected in an objective lens 24, and a fluorescence image is focused (formed) on an input plane 26a (the smaller end) of an image fiber 26. Similarly, the transmitted light image from the particle is focused (formed) on the input plane 26a of the image fiber 26. The fluorescence image of the output plane 26b of the image fiber 26 is enlarged more than the image of the input plane 26a, and its fluorescence image If is focused (formed) on the input plane (photoelectric plane) of an image intensifier 34 through a dichroic mirror 28, a relay lens 30, and a filter 32. The wavelength characteristics of the dichroic mirror 28 and filter 32 are matched with the wavelength of laser light and the fluorescence wavelength spectrum. That is, the dichroic mirror 28 and filter 32 transmit the light longer than the wavelength of the laser light.

Figure 5:
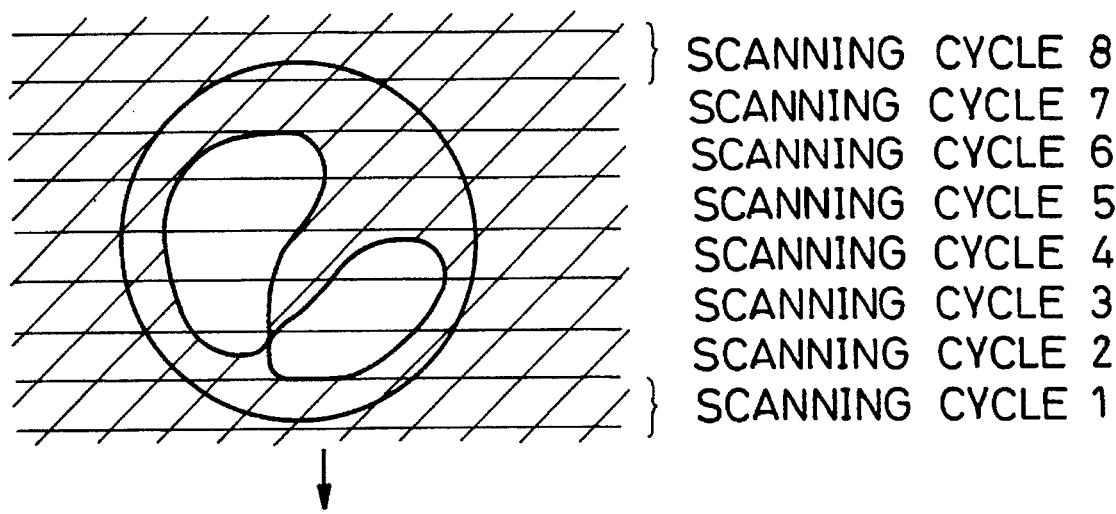
FIG. 5 is a diagram showing an example of fluorescence image If in particle scanning.
Figure 6:
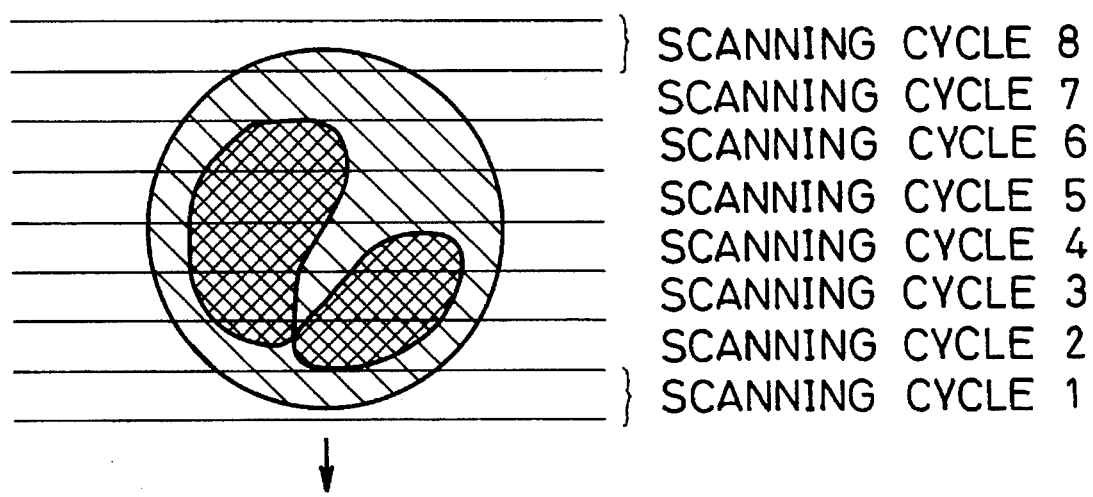
FIG. 6 is a diagram showing an example of transmitted light image It in particle scanning.
Figure 7:
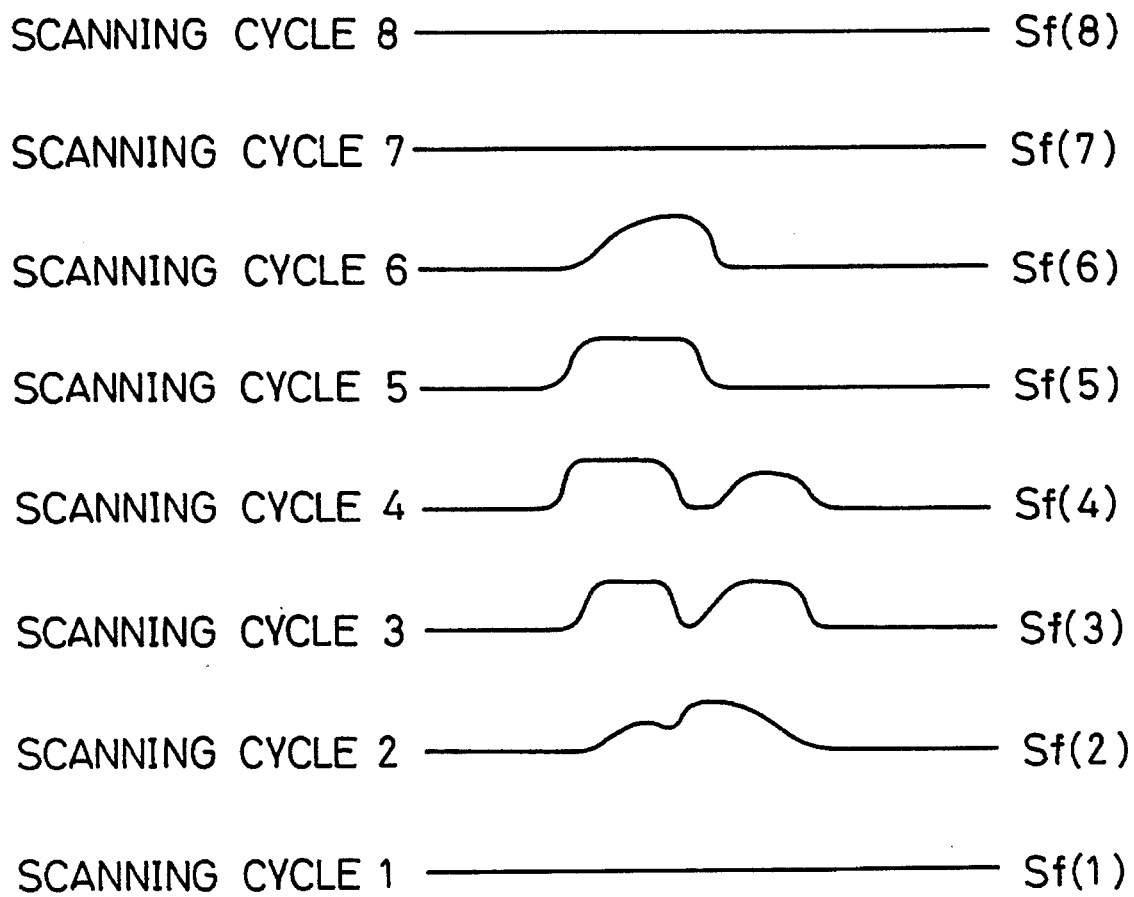
FIG. 7 is a wave form chart showing an example of fluorescence detection signal Sf (i) by line sensor.

The fluorescence image multiplied tens of thousands of times by the image intensifier 34 is scanned by a one-dimensional image sensor, for example, a line sensor 36, and a detection signal Sf (i) as shown in FIG. 7 is obtained, in which i refers to a scanning cycle number. FIG. 5 shows a fluorescence image If, and FIG. 6 shows a transmitted light image It.

As shown in FIG. 4, in the laser beam irradiation area A1, the imaging area A2 by the line sensor 36 comes in the central position of the irradiation area A1, and the fluorescence excited when the particle 22 crosses the laser irradiation area A1 is focused on the line sensor 36. This fluorescence image is scanned by the line sensor 36 in scores of microseconds, and signals are sequentially issued depending on the exposure quantity in each pixel (picture element) for a period of scores of microseconds. The time required for output of a signal to all pixels is determined by the number of pixels and the shift clock frequency, and, for example, in the case of 256 pixels and a 12 MHz clock, it is about 20 μsec. This time is the time required for scanning particle images in one line, that is, the scanning cycle.

Figure 8:
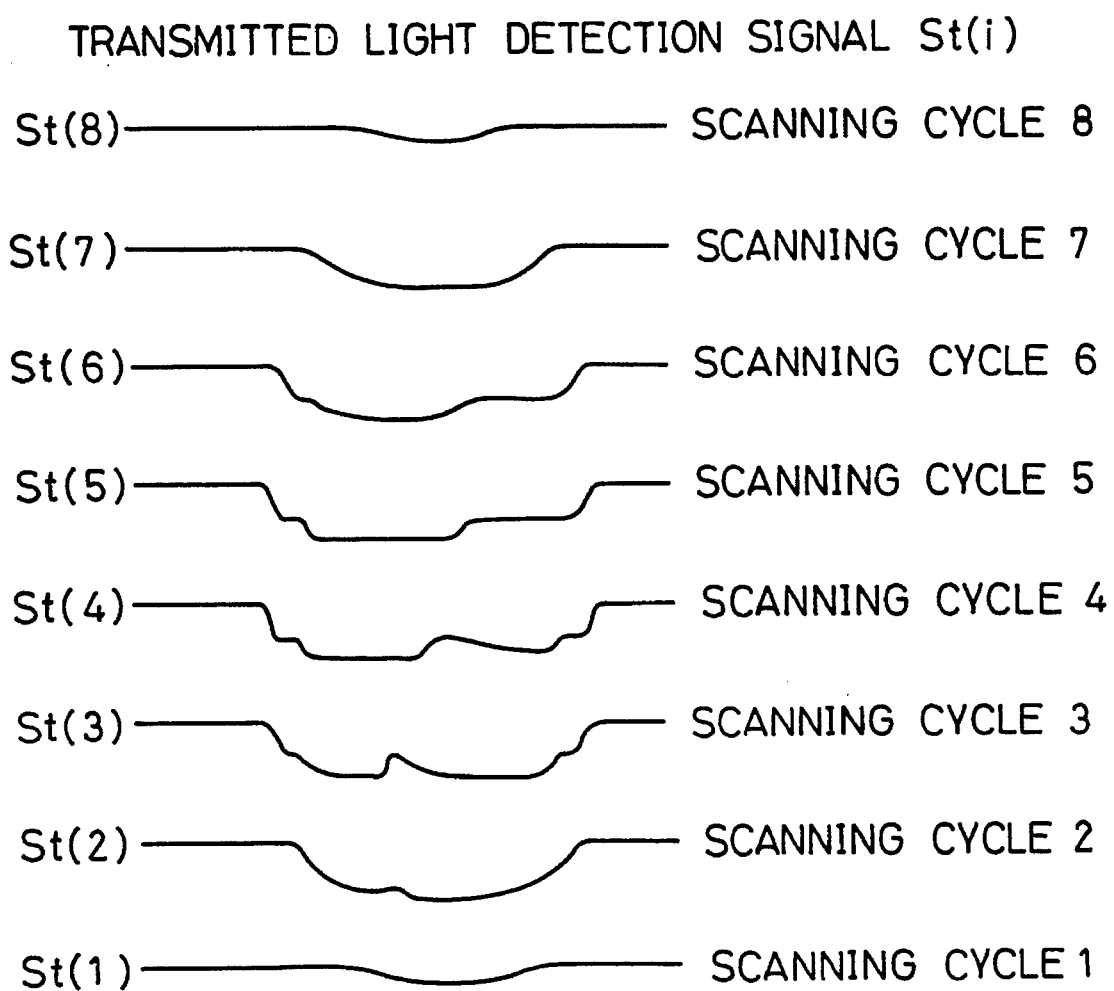
FIG. 8 is a wave form chart showing an example of transmitted light detection signal St (i) by line sensor.

On the other hand, the particle transmitted light image It reflected by the dichroic mirror 28 is focused by the relay lens 38 on a second one-dimensional image sensor, for example, a line sensor 40, and a detection signal as shown in FIG. 8 is obtained. By the particle crossing the laser irradiation region, the exposure to the line sensor is blocked, and signals corresponding to the exposure quantity of each pixel are sequentially issued.

Figure 9:
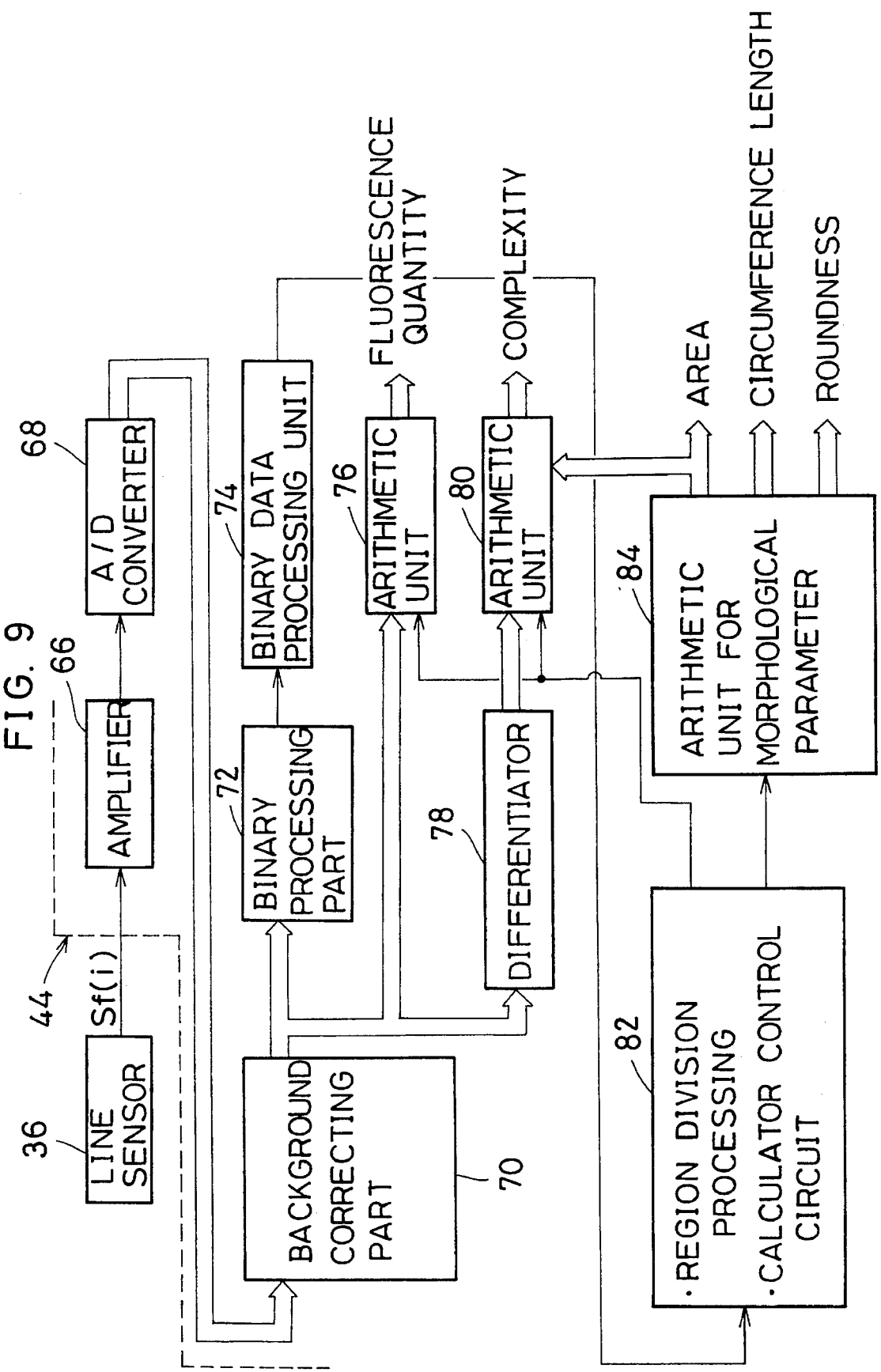
FIG. 9 is a block diagram showing an example of line sensor detection signal processing circuit.

The fluorescence detection signal Sf (i) obtained from the line sensor 36 is processed by a signal processor 44 having signal processing blocks as shown in FIG. 9, and the parameters of individual particles, such as fluorescence quantity, area (nuclear area), roundness, complexity and fluorescence luminance distribution width of fluorescent emission portion can be calculated (obtained) in real time.

The transmitted light detection signal obtained by the line sensor 40 is similarly processed separately by the signal processor 46, and the absorption quantity of individual particles, area, roundness and complexity of each particle, and others can be calculated. The circuit in FIG. 9 is described later.

With these determined parameters, it is also possible to calculate the ratio occupied by the nucleus in the entire cell, and fluorescence intensity and absorbance per unit area, and others (not shown in FIG. 9).

In this embodiment, in the light reception system, the tapered image fiber 26 having an image enlarging function is used, and therefore the multiplication factor of the objective lens 24 may be lowered accordingly, so that the focal depth may be deepened, and hence the image adjusted more in focus than before and the entire particle may be formed on the line sensor.

Instead of the taper type, it is also possible to deepen the focal depth by using a straight type image fiber.

Embodiment 2

Figure 3:
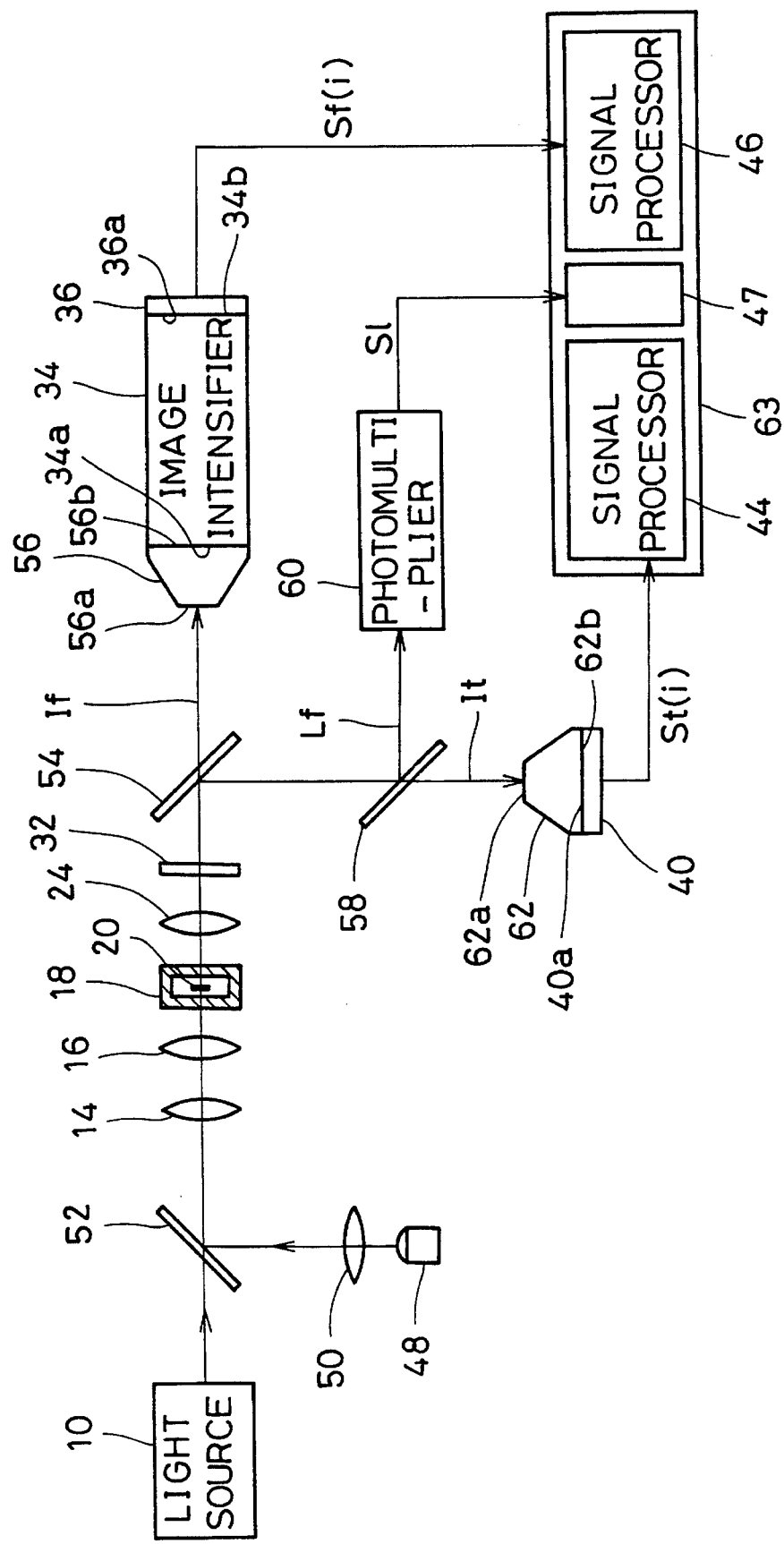
FIG. 3 is a schematic diagram (plan) showing another embodiment of an apparatus for analyzing particles of the present invention.

FIG. 3 shows an apparatus for analyzing particles in Embodiment 2. In this embodiment, as the light source for obtaining a transmitted light image of the particle, another light source 48 is used, for example, a super-luminescence diode (SLD) of low coherency, and it is intended to obtain particle images of less coherence (interference) fringe as compared with Embodiment 1.

The light from the first light source (laser light source) 10 for fluorescence excitation and the light emitted from the second light source 48 for obtaining a transmitted light image and passing through a collimator lens 50 are combined in a dichroic mirror 52, and by the cylindrical lens 14 and condenser lens 16, the light is finely reduced the same as in the area A1 in FIG. 4 and emitted to the flat sample flow 20 in the flow cell 18. Since the first light source 10 and the second light source 48 differ in wavelength, it does not matter if the irradiation regions by the two light sources overlap, and it is possible to form the two light sources on the same optical axis.

The fluorescence obtained as the particle crosses the laser irradiation region is collected by the objective lens 24, and the light due to the light source 10 is cut off by the filter 32, and only the light in the fluorescence of waveform region transmits the dichroic mirror 54, and the fluorescence image If is focused (formed) on the input plane 56a (the smaller end) of the image fiber 56. The output plane 56b of the image fiber 56 is in tight contact with the photoelectric plane (input plane) 34a of the image intensifier 34, and the output plane 34b of the image intensifier 34 is in tight contact with the light reception plane 36a of the line sensor 36. In this way, the particle fluorescence image If is enlarged and multiplied, and is focused on the line sensor 36, thereby obtaining a fluorescence detection signal Sf (i) as shown in FIG. 7.

In this embodiment, dichroic mirror 58 and photomultiplier 60 are added so that the fluorescence Lf other than in the wavelength region detected by the line sensor 36 may be detected as fluorescence intensity of the entire particle.

The particle transmitted light by the second light source 48 is reflected by the dichroic mirror 54, and passes through another dichroic mirror 58 and enters the input plane 62a of the image fiber 62, and the transmitted light image It is formed. The output plane 62b of the image fiber 62 is in tight contact with the light reception plane 40a of the line sensor 40. In this way, the particle transmitted image is focused (formed) on the line sensor 40, and the transmitted light detection signal St (i) as shown in FIG. 8 are obtained.

Thus obtained detection signals Sf (i), Lf, St (i) are processed by a signal processor 63, and various parameters as mentioned above are calculated (obtained) in real time.

Embodiment 3

FIG. 10 shows an apparatus for analyzing particles according to Embodiment 3. In this embodiment, modifying Embodiment 2, the irradiation method of excitation light by the light source 10 is changed, and as compared with Embodiment 2, fluorescence images of higher S/N ratio (signal-to-noise ratio) can be scanned. The reference numbers in FIG. 10 are the same as in Embodiment 2 (FIG. 3).

An example of a signal processing circuit shown in FIG. 9 is briefly explained below. First, an example of a fluorescence detection signal Sf (i) in FIG. 7 is explained. The detection signal Sf (i) from the line sensor 36 is first amplified by an amplifier 66, and is A/D converted by a A/D converter 68 at the same frequency as the shift clock of the line sensor. The data is then fed to a background correcting part 70 to undergo background correction processing. In the background correcting part 70, the data for one line obtained while the particle is not crossing the line sensor imaging area A2 (background data) is preliminarily stored in memory, and the difference between the stored data and the A/D converted data obtained during measurement is calculated in real time. The purpose of this processing is to correct uneven irradiation intensity by laser light or fluctuations (dispersions) of sensitivity of each pixel of the line sensor.

The corrected data is fed into a binary processing part 72 in order to cut out (form) the signal bounds corresponding to the fluorescent image, and is compared with the data at a certain proper reference (standard) level, and is formed into binary notation. The binary data is fed into a binary data processing unit 74 to be deprived (removed) of small dust signals, and the binary data bounds corresponding to an individual particle is divided. That is, this is the pretreatment for region division. Herein, the region division processing is to cut out (form) the bounds (timing) of the binary data corresponding to one particle appearing in a continuous plural line data, and this processing is necessary for creating timing control signals for calculating the fluorescent quantity and morphological information of individual particles in real time.

By the region division processing and control signal from calculation control circuit 82, arithmetic units 76, 80, 84 for calculating the fluorescent quantity, complexity, roundness and other morphological information is controlled, and these parameters are calculated in real time for each particle 22 passing the line sensor imaging area A2. Numeral 78 is a differentiator.

In the present invention, in order to obtain fluorescence images of high S/N ratio small in effects of excitation light or stray light, the image intensifier 34 for multiplying the fluorescence may be operated, by limiting the operation time to the period of scanning cycles where transmitted light detection signal St (i) by the line sensor 40 are being obtained. For this purpose, an image intensifier with a shutter function may be used.

Being thus constructed, the present invention brings about the following effects.

(1) In addition to the scattered light intensity, fluorescence intensity and other optical features of particles obtained in the conventional flow cytometer, the morphological information of the particles, area and roundness, luminance distribution and other information about fluorescent image can also be obtained in real time, so that particles may be analyzed at higher precision.

(2) Since a particle image is canned by a one-dimensional image sensor (line sensor), although the sample flow velocity cannot be accelerated, more particles can be analyzed by passing the sample flow flatly and broadly (widely).

(3) By using an image fiber in the light detection system by a one-dimensional image sensor (line sensor), the focal depth may be deepened, and if the sample flow is somewhat thick, in-focus particle images can be formed on the line sensor, so that more precise information about particle images may be obtained.

(4) When the present invention is applied to a cell sorter, as the information for judging the sorting, the particle morphological information, area, roundness and other information as to the fluorescent image may be added aside from the conventional parameters such as scattered light intensity and fluorescence intensity, so that particles may be separated more precisely.

Having described preferred embodiments of the present invention wit reference to the accompanying drawings, it is to be understood that the present invention is not limited to those precise embodiments, and that various changes and modifications may be effected therein by one skilled in the art without departing from the scope or spirit of the present invention as defined in the appended claims.

What is claimed is:

1. An apparatus for analyzing particles by discharging a sample liquid containing particles to be detected from a nozzle of a flow cell, passing a sheath liquid around the sample liquid to form a sheath flow, emitting light to the sample liquid flow, detecting the light from the particles, and analyzing the particles according to detection signals associated with the detected light, comprising:

said flow cell for forming said sample liquid flow as a flat flow, thin in thickness and broad in width;

a light source for said emitting light emitted to said sample liquid;

an image intensifier for intensifying the fluorescence image of the particles excited by the light and emitted from the broad side of said sample liquid flow on an input plane of said image intensifier;

a one-dimensional image sensor extended at an output plane side of said image intensifier in a vertical direction to the flow direction of particles, for scanning a fluorescence image amplified by said image intensifier, and issuing an imaging signal Sf (i) at every scanning; and signal processing means for performing at least one of processing signals and operating on the imaging signals SF (i) from thr one-dimensional image sensor.

2. An apparatus for analyzing particles of claim 1, further comprising:

a second one-dimensional image sensor, said second one dimensional image sensor extending in a vertical direction to the flow direction of the particles, for scanning the particle transmitted light images og the broader side of said sample liquid flow, and issuing an imaging signal St (i) in every scanning i.

3. An apparatus for analyzing particles of claim 2, further comprising: means for lowering the coherency of said emitting light.

4. An apparatus for analyzing particles by discharging a sample liquid containing particles to be detected from a nozzle of a flow cell, passing a sheath liquid around the sample liquid to form a sheath flow, emitting light to the sample liquid flow, detecting the light from the particles, and analyzing the particles according to detection signals associated with the detected light, comprising:

said flow cell for forming said sample liquid flow as a flat flow, thin in thickness and broad in width;

a first light source for emitting first light to said sample liquid;

an image intensifier for intensifying the fluorescence image of the particles excited by the light emitted by said first light source and emitted from the broad side of said sample liquid flow on an input plane of said image intensifier;

a first one-dimensional image sensor extended at the output plane side of said image intensifier for scanning a fluorescence image amplified by said image intensifier and issuing an imaging signal Sf (i) in every scanning i;

a second light source for emitting second light different in wavelength from the first light to said sample liquid;

a second one-dimensional image sensor extended in a vertical direction to the particle flow direction for scanning the particle transmitted light image of the broader side of said sample liquid flow and issuing an imaging signal St (i) in every scanning i; and signal processing means for performing at least one of processing signals and operating on the basis of the imaging signal Sf (i) from said first one-dimensional image sensor and the imaging signal St (i) from said second one-dimensional image sensor.

5. An apparatus for analyzing particles of claim 4, wherein said second light source is a light source for emitting low coherency light.

6. An apparatus for analyzing particles of claim 2, wherein the signal St (i) from said one-dimensional image sensor is processed, and said image intensifier is controlled so as to be in an active state only while a particle is passing through the imaging region A2.

7. An apparatus for analyzing particles of claim 4, wherein the signal St (i) from said one-dimensional image sensor is processed, and said image intensifier is controlled so as to be in an active state only while a particle is passing through the imaging region A2.

* * * * *

UNITED STATES PATENT AND TRADEMARK OFFICE
CERTIFICATE OF CORRECTION

PATENT NO. : 5,469,251
DATED : November 21, 1995
INVENTOR(S) : Tokihiro Kosaka et al It is certified that error appears in the above-indentified patent and that said Letters Patent is hereby corrected as shown below:

Claim 1, column 9, line 15, "thr" should be "the".

Claim 2, column 9, line 21, "og" should be "of".

Signed and Sealed this

Twenty-eighth Day of May, 1996

Attest:

BRUCE LEHMAN

*Attesting Officer*   *Commissioner of Patents and Trademarks*